United States Patent [19]

Peet et al.

[11] 4,064,348

[45] Dec. 20, 1977

[54] 2-CYCLOALKYL-AMINO-2-OXAZOLINES

[75] Inventors: Norton P. Peet; Shyam Sunder, both of Midland, Mich.

[73] Assignee: The Dow Chemical Company, Midland, Mich.

[21] Appl. No.: 740,636

[22] Filed: Nov. 10, 1976

Related U.S. Application Data

[63] Continuation-in-part of Ser. No. 624,364, Oct. 21, 1975, abandoned.

[51] Int. Cl.² .......................................... C07D 413/04
[52] U.S. Cl. ............................ 544/137; 260/293.67; 260/307 F; 424/248.56; 424/267; 424/272; 71/88; 71/94
[58] Field of Search ................ 424/364; 260/247.5 E, 260/293.67, 307 F

[56] References Cited

U.S. PATENT DOCUMENTS 3,945,998  3/1976  Anderson et al. ............... 260/307 F

OTHER PUBLICATIONS

Tomolia et al. "J. Org. Chem." vol. 34, 1400 (1969).

*Primary Examiner*—Henry R. Jiles
*Assistant Examiner*—R. W. Ramsuer
*Attorney, Agent, or Firm*—James W. Ambrosius

[57] ABSTRACT

Novel 2-cycloalkylamino-2-oxazolines and their salts are described which are biologically active. Member compounds exhibit useful activity as CNS-depressants, CNS-stimulants, platelet aggregation inhibitors, fungicides, and herbicides.

12 Claims, No Drawings

2-CYCLOALKYL-AMINO-2-OXAZOLINES

CROSS REFERENCE TO RELATED APPLICATION

The present application is a continuation-in-part of applicants' copending application Ser. No. 624,364 filed Oct. 21, 1975 now abandoned.

SUMMARY OF THE INVENTION

The present invention is directed to 2-amino-2-oxazolines represented by either of the following formulas:

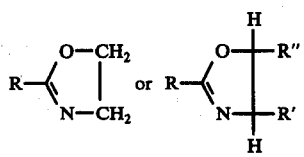

wherein R represents
1-pyrrolidino,
1-piperidino,
1-(2-methyl)piperidino,
1-(3-methyl)piperidino,
1-(4-methyl)piperidino,
4-morpholino,
1-hexamethyleneimino,
1-(2,6-dimethyl)piperidino, and
1-heptamethyleneimino;

R' represents hydrogen or an alkyl group of from 1 to about 4 carbon atoms;

and R" represents hydrogen, an alkyl group of from 1 to about 4 carbon atoms, or phenyl with the proviso that when R' is hydrogen R" is other than hydrogen and when R' is alkyl R" is other than alkyl.

Pharmaceutically acceptable salts of the above compounds are included in this invention.

As employed herein, the phrase pharmaceutically-acceptable salts refers to non-toxic acid addition salts of the oxazoline compound, the anions of which are relatively innocuous to animals at dosages consistent with good pharmacodynamic activity so that the beneficial effects of the free base are not vitiated by side effects ascribable to the anions. Pharmaceutically-acceptable salts include those derived from mineral acids such as hydrochloric, hydrobromic, sulfuric, and nitric acids and from organic acids such as acetic, lactic, maleic, succinic, fumaric, glutaric, citric, malic, p-toluene-sulfonic, and tartaric acids, and the like.

The compounds of the present invention are normally crystalline solids or oils. They are normally soluble both in organic solvents and in water. Member compounds of the invention have been found to exhibit useful activity as CNS-depressants, CNS-stimulants, platelet aggregation inhibitors, and blood cell anti-sickling agents. Additionally certain members have been found to display anti-fungal activity and also have been shown to be useful in various agricultural applications such as the control and killing of noxious weeds and plant parasites. Each of the disclosed species of the invention has shown an activity in one or more of the above tested areas. It is recognized, however, that not all of the compounds of the invention exhibit the same degree of activity nor are all of the species active in all the areas.

PRIOR ART

Although oxazolines are not new in the art, oxazolines having cycloamino moieties in the 2-position have not been extensively investigated. See D. A. Tomalia, et al, *J. Org. Chem.*, 34, 1400 (1969). Piperazine derivatives are described in the German Offenlegungsschrift No. 2,205,815. Only a limited number of 2-oxazolines bearing a dialkylamino group in the 2-position are known. G. I. Poos, et al. *J. Med. Chem.*, 6, 266 (1963); G. I. Poos, U.S. Pat. No. 3,161,650; D. L. Trepanier, et al., *J. Med. Chem.*, 13, 729 (1970); and *Chem. Abstracts,* 75:151,714K. The preparation of oxazolines from aziridinylureas and hydroxyethylureas is the standard method of making these compounds. J. A. Frump, *Chem Reviews,* 71, 483 (1971); H. Bestian, *Ann Chemie,* vol. 566, p. 210 (1950). The compounds of the present invention owe their novelty to the cycloamino moieties in the 2-position. Several aziridinylureas which serve as intermediates for the preparation of the 2-amino-2-oxazolines are known. See H. Bestian, *Ann Chemie,* vol. 55, (1950) pp. 230–231.

DETAILED DESCRIPTION OF THE INVENTION

Compounds of the present invention unsubstituted in the oxazoline ring can be prepared by isomerizing the corresponding aziridinylurea in the presence of a catalyst (usually sodium iodide). The aziridinylurea, in turn, is prepared by reacting ethyleneimine with a carbamoyl chloride. The two step reaction is illustrated below.

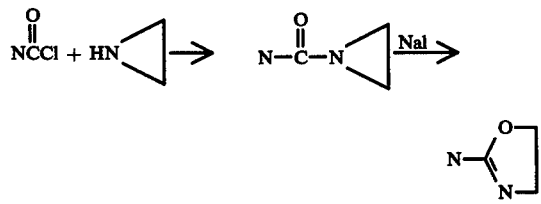

Carbamoyl chlorides used to prepare the present compounds can be obtained commercially or if not commercially available are prepared by reacting a predetermined amine with excess phosgene in either toluene or ethyl acetate.

Compounds bearing substituents on the oxazoline ring are prepared by reacting a carbamoyl chloride with an amino alcohol to give the corresponding hydroxyethylurea, which is cyclized by treatment with thionyl chloride as shown below.

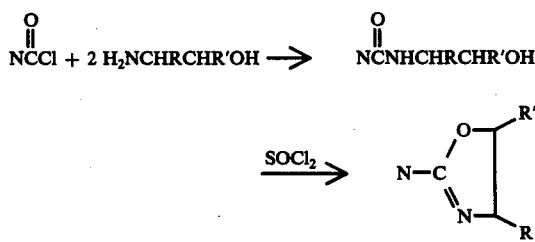

Although this latter method can be used for the preparation of the unsubstituted oxazolines as well, the method used for the unsubstituted oxazolines is not readily applicable to the preparation of the substituted oxazolines, since ethyleneimine bearing the necessary substituents is not readily available.

The substituted oxazolines are pharmacodynamically active, and they are particularly active as platelet aggregation inhibitors and central nervous system stimulants.

4-(4-Ethyl-4,5-dihydro-2-oxazolyl)-4-morpholine (Example 24) has also shown utility as an anti-sickling agent. Unsubstituted oxazolines tend to be less active pharmacodynamically although antiplatelet aggregation and central nervous system-stimulant activity have been recognized in several members. Unsubstituted oxazolines have also shown activity as anti-sickling agents. Both substituted and unsubstituted oxazolines have shown useful activity in the agricultural area. Various compounds exhibit utility as pesticidal, fungicidal, antimicrobial, and weed control agents.

Following the procedure as set forth directly hereinbefore, a number of unsubstituted oxazolines were prepared having the following general formula:

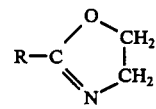

Table I summarizes the results from these studies.

TABLE I

| Example No. | R | MP/BP (mm),° C | % Yield | Empirical formula | Mol. Wt. |
|---|---|---|---|---|---|
| 2 | 1-pyrrolidino | 81–82(5.0) | 65.0 | $C_7H_{12}N_2O$ | 140.19 |
| 3 | 4-morpholino | 101–102 | 80.5 | $C_7H_{12}N_2O_2$ | 156.18 |
| 4 | 1-(2-Me)piperidino | 89–90(1.3) | 76.6 | $C_9H_{16}N_2O$ | 168.23 |
| 5 | 1-(3-Me)piperidino | 88–90(1.6) | 75.0 | $C_9H_{16}N_2O$ | 168.23 |
| 6 | 1-(4-Me)piperidino | 87–88(1.3) | 71.0 | $C_9H_{16}N_2O$ | 168.23 |
| 7 | 1-(2,6-diMe)-piperidino | 74–76 | 50.0 | $C_{10}H_{18}N_2O$ | 182.26 |
| 8 | 1-hexamethyleneimino | 87–88(1.0) | 38.0 | $C_9H_{16}N_2O$ | 168.23 |
| 9 | 1-heptamethylene-imino | 106–107(1.5) | 35.0 | $C_{10}H_{18}N_2O$ | 182.26 |

*Crude yield

Preparation of Unsubstituted 2-Cycloalkylamino-2-oxazoline

EXAMPLE 1 a. General Preparation of Aziridinylurea Intermediates

A 0.1-mol quantity of a selected carbamoyl chloride is dissolved in 50–100 ml of an inert, organic solvent such as benzene, methylene chloride or chloroform. This solution is then added dropwise, with icebath cooling, to a solution of 0.11 mol of ethyleneimine plus 0.11 mol of a hydrogen chloride acceptor, preferably a trialkylamine such as triethylamine, in 50–100 ml of an inert, organic solvent. Larger excesses of the latter two reagents can be employed. After 1–12 hr. of stirring, the reaction slurry is filtered to remove the insoluble trialkylamine hydrochloride. The filtrate is concentrated and (1) the pure solid is collected or (2) the resulting oil is distilled under reduced pressure, preferably 1 mm or less, to minimize thermal conversion of the aziridinylurea to 2-amino-2-oxazoline.

b. General Preparation of the Unsubstituted 2-Cycloalkylamino-2-oxazoline

A 0.1-mol quantity of an aziridinylurea prepared as described in (a) above is dissolved in a 50–200 ml volume of a polar, organic solvent, preferably acetonitrile. A 0.5–2.0-g quantity of sodium iodide is added as a catalyst for the rearrangement. Progress of the reaction is conveniently followed by vapor phase chromatography. When the rearrangement is complete (usually 1–44 hr.), the catalyst is removed by filtration, the solvent removed by evaporation, and (1) the resulting solid is recrystallized from an appropriate solvent or solvents (i.e., acetonitrile, hexane, or methylene chloride-hexane), or (2) the resulting oil is distilled under reduced pressure, preferably 1 mm or less, to minimize product polymerization.

Alternatively, these unsubstituted oxazolines can be generated from the appropriate N-(2-hydroxyethyl)-ureas by treatment with a cyclizing agent (i.e., thionyl chloride), as described for similar compounds having substitutions on the oxazoline ring.

EXAMPLE 10

Preparation of 4-(4,5-dihydro-2-oxazolyl)-morpholine. See Example 3, Table I.

a. Preparation of Aziridinylurea Intermediate

A 29.92 gram quantity of morpholine carbonyl chloride in 50 ml. of benzene was added slowly over a 30 minute period to a solution of 9.48 grams of ethyleneimine and 22.26 grams of triethylamine in 100 ml. of benzene. The reaction mixture was stirred for 30 minutes and filtered to remove 26.82 grams of triethylamine hydrochloride. The filtrate was concentrated to leave 32.75 grams of the crude aziridinylurea, 4-(1-aziridinylcarbonyl)morpholine. Distillation of the resulting crude urea gave 28.84 grams of purified aziridinylurea intermediate.

b. Preparation of the Unsubstituted Oxazoline

A 12.00 gram quantity of the aziridinylurea and 2.00 grams of sodium iodide in 120 ml. of acetonitrile were heated at reflux for 5 days and 15 hours. The reaction mixture was eluted through 50 grams of alumina in a column slurry-packed with acetonitrile. The column was washed with 300 ml. of acetonitrile. Concentration of the eluent left 12.06 grams of white solid. This solid was recrystallized from hexane to give 9.67 grams of 4-(4,5-dihydro-2-oxazolyl)morpholine.

Preparation of Substituted 2-Cycloalkylamino-2-oxazoline

EXAMPLE 11 a. General Preparation of Hydroxyethylurea Intermediate

A 0.1 mol quantity of a selected amino alcohol and a 0.1 mol quantity of a trialkylamine, preferably triethylamine, are dissolved in ca. 200 ml of an inert solvent, preferably $CH_2Cl_2$. The resulting solution is cooled in an icebath. A 0.1 mol quantity of the appropriate carbamoyl chloride in ca. 20 ml of the inert solvent is added and the reaction mixture is stirred at 25° C. for 10 hrs. The mixture is washed with water and/or saturated $K_2CO_3$ solution, dried ($Na_2SO_4$) and concentrated to leave either a clear liquid or a white solid. This is recrystallized from ethyl alcohol, methylene chloride, ethyl alcohol-ethyl ether or methylene chloride-ethyl ether.

b. General Preparation of the Substituted 2-Cycloalkylamino-2-oxazoline

A 0.05 mol quantity of a hydroxyethylurea prepared as described in (a) above is dissolved in ca. 200 ml of an inert solvent, preferably methylene chloride, and cooled in an icebath. A 0.05 mol quantity of thionyl chloride in ca. 20 ml of the inert solvent is added and the yellow solution is stirred at 25° C. for 30 minutes, heated at reflux for 30 minutes, and allowed to stand at 25° C. for 10 hrs. before being concentrated to dryness. The concentrate is dissolved in $H_2O$ and made basic by the addition of saturated potassium carbonate ($K_2CO_3$) solution. Extraction of the mixture with the inert solvent and drying with sodium sulfate ($Na_2SO_4$) and concentrating the separated organic layer leaves a liquid which is distilled under reduced pressure.

Following the procedure as set forth directly hereinbefore, a number of substituted oxazolines were prepared having the general formula:

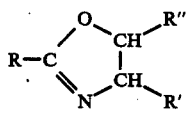

Table II summarizes the results from these studies.

The organic layer was then filtered and evaporated to a small volume. The hydroxyethylurea, N-(1-methyl-2-phenyl-2-hydroxyethyl)-4-morpholine carboxamide, was filtered off as a white solid and recrystallized from $CH_2Cl_2$.

b. Preparation of the Substituted 2-Cycloalkylamino-2-oxazoline

A solution of 10.6 grams of the hydroxyethylurea in 200 ml. of $CH_2Cl_2$ was cooled to 0° C. Thionyl chloride (5.36 grams) dissolved in 20 ml. of $CH_2Cl_2$ was added, and the mixture was heated at reflux temperature for 30 minutes. The mixture was left at room temperature for 64 hours. The solvent was evaporated under vacuum to leave a yellow gum. This material was dissolved in water. Concentrated $K_2CO_3$ solution was added to make the solution basic. The 4-(4,5-dihydro-4-methyl-5-phenyl-2-oxazolyl)morpholine separated out as an oil. The oil was dissolved in $CH_2Cl_2$, washed with water, and dried over anhydrous $Na_2SO_4$. The solution was filtered and evaporated to an oil.

A number of the compounds of the present invention are useful in preventing aggregation of blood platelets. Activity is indicated by challenging with adenosine 5'-diphosphate (ADP) mice which have received an oral dose of the test compound. Emboli formed in the capillary beds of unprotected mice following administration of ADP results in a stroke-like response that prevents the mice from staying on an inclined screen.

TABLE II

| Example No. | R | R' | R'' | MP/BP (mm),° C | % Yield | Recrystn. Solvent | Empirical Formula | Mol. Wt. |
|---|---|---|---|---|---|---|---|---|
| 12 | 1-pyrrolidino | H | $CH_3$ | 67–68(0.8) | 39 | | $C_8H_{14}N_2O$ | 154.2 |
| 13 | 1-piperidino | H | $CH_3$ | 61–62(0.3) | 67 | | $C_9H_{16}N_2O$ | 168.23 |
| 14 | 1-(2-Me)piperidino | H | $CH_3$ | 80–82(0.35) | 50 | | $C_{10}H_{18}N_2O$ | 182.26 |
| 15 | 1-(3-Me)piperidino | H | $CH_3$ | 68(0.5) | 58 | | $C_{10}H_{18}N_2O$ | 182.26 |
| 16 | 1-(4-Me)piperidino | H | $CH_3$ | 65–67(0.25) | 67 | | $C_{10}H_{18}N_2O$ | 182.26 |
| 17 | 4-morpholino | H | $CH_3$ | 65–67(0.2) | 69 | | $C_8H_{14}N_2O_2$ | 170.21 |
| 18 | 1-hexamethyleneimino | H | $CH_3$ | 75–76(0.7) | 62 | | $C_{10}H_{18}N_2O$ | 182.26 |
| 19 | 1-pyrrolidino | $C_2H_5$ | H | 64–66(0.3) | 38 | | $C_9H_{16}N_2O$ | 168.23 |
| 20 | 1-piperidino | $C_2H_5$ | H | 86–88(0.3) | 58 | | $C_{10}H_{18}N_2O$ | 182.26 |
| 21 | 1-(2-Me)piperidino | $C_2H_5$ | H | 82(0.4) | 55 | | $C_{11}H_{20}N_2O$ | 196.29 |
| 22 | 1-(3-Me)piperidino | $C_2H_5$ | H | 76–77(0.5) | 60 | | $C_{11}H_{20}N_2O$ | 196.29 |
| 23 | 1-(4-Me)piperidino | $C_2H_5$ | H | 75–77(0.25) | 68 | | $C_{11}H_{20}N_2O$ | 196.29 |
| 24 | 4-morpholino | $C_2H_5$ | H | 71–73(0.4) | 57 | | $C_9H_{16}N_2O_2$ | 184.23 |
| 25 | 1-hexamethyleneimino | $C_2H_5$ | H | 84–87(0.3) | 70 | | $C_{11}H_{20}N_2O$ | 196.29 |
| 26 | 1-pyrrolidino | H | $C_6H_5$ | 134–135(0.5) | 30 | | $C_{13}H_{16}N_2O$ | 216.27 |
| 27 | 1-piperidino | H | $C_6H_5$ | 165–167(1.4) | 84 | | $C_{14}H_{18}N_2O$ | 230.30 |
| 28 | 1-(2-Me)piperidino | H | $C_6H_5$ | 145–146(0.5) | 24 | | $C_{15}H_{20}N_2O$ | 244.33 |
| 29 | 1-(3-Me)piperidino | H | $C_6H_5$ | 144–146(0.5) | 41 | | $C_{15}H_{20}N_2O$ | 244.33 |
| 30 | 1-(4-Me)piperidino | H | $C_6H_5$ | 140–142(0.2) | 55 | | $C_{15}H_{20}N_2O$ | 244.33 |
| 31 | 4-morpholino(HCl) | H | $C_6H_5$ | 144–145 | 48 | $CH_2Cl_2$-$Et_2O$ | $C_{13}H_{16}N_2O_2 \cdot HCl$ | 268.72 |
| 32 | 1-hexamethyleneimino | H | $C_6H_5$ | 157–158(1.1) | 46 | | $C_{15}H_{20}N_2O$ | 244.33 |
| 33 | 1-pyrrolidino | $CH_3$ | $C_6H_5$ | 147(1.2) | 94* | | $C_{14}H_{18}N_2O$ | 230.30 |
| 34 | 1-piperidino | $CH_3$ | $C_6H_5$ | 130–131(0.3) | 87 | | $C_{15}H_{20}N_2O$ | 244.33 |
| 35 | 1-(2-Me)piperidino | $CH_3$ | $C_6H_5$ | 144–145(0.7) | 61 | | $C_{16}H_{22}N_2O$ | 258.35 |
| 36 | 1-(3-Me)piperidino | $CH_3$ | $C_6H_5$ | 144–146(0.3) | 86 | | $C_{16}H_{22}N_2O$ | 258.35 |
| 37 | 1-(4-Me)piperidino | $CH_3$ | $C_6H_5$ | 143–145(0.3) | 52 | | $C_{16}H_{22}N_2O$ | 258.35 |
| 38 | 4-morpholino | $CH_3$ | $C_6H_5$ | 133–134(0.2) | 84 | | $C_{14}H_{18}N_2O_2$ | 246.30 |
| 39 | 1-hexamethyleneimino | $CH_3$ | $C_6H_5$ | 144–146(0.4) | 82 | | $C_{16}H_{22}N_2O$ | 258.35 |

*Crude yield

EXAMPLE 40

Preparation of 4-(4,5-dihydro-4-methyl-5-phenyl-2-oxazolyl)morpholine. See Example 38, Table II.

a. Preparation of Hydroxyethylurea Intermediate

A solution of 15.2 grams of norephedrine in 200 ml. of methylene chloride ($CH_2Cl_2$) was cooled to 0°–5° C. To this 11.0 grams of triethylamine was added with stirring. To the stirred mixture a solution of 14.9 grams of morpholine carbonyl chloride in 10 ml. of $CH_2Cl_2$ was added dropwise. The mixture was then stirred for 2 hours and left to stand at room temperature for 16 hours. The mixture was washed with water and the organic layer was dried over anhydrous sodium sulfate.

Table III lists those compounds of the present invention which inhibit the aggregation of blood platelets in mice at an oral dosage of 60 mg/kg.

Table III

| | | Platelet Aggregation Inhibitors | | |
|---|---|---|---|---|
| Table | Example # | R | R' | R'' |
| I | 4 | 1-(2-Me)piperidino | H | H |
| | 7 | 1-(2,6-diMe)piperidino | H | H |
| | 9 | 1-heptamethyleneimino | H | H |
| II | 13 | 1-piperidino | H | $CH_3$ |
| | 14 | 1-(2-Me)piperidino | H | $CH_3$ |
| | 18 | 1-hexamethyleneimino | H | $CH_3$ |
| | 21 | 1-(2-Me)piperidino | $C_2H_5$ | H |
| | 22 | 1-(3-Me)piperidino | $C_2H_5$ | H |
| | 26 | 1-pyrrolidino | H | $C_6H_5$ |
| | 27 | 1-piperidino | H | $C_6H_5$ |

Table III-continued

| Platelet Aggregation Inhibitors | | | | |
|---|---|---|---|---|
| Table | Example # | R | R' | R" |
| | 28 | 1-(2-Me)piperidino | H | C$_6$H$_5$ |
| | 30 | 1-(4-Me)piperidino | H | C$_6$H$_5$ |
| | 31 | 4-morpholino | H | C$_6$H$_5$ |
| | 32 | 1-hexamethyleneimino | H | C$_6$H$_5$ |
| | 33 | 1-pyrrolidino | CH$_3$ | C$_6$H$_5$ |
| | 36 | 1-(3-Me)piperidino | CH$_3$ | C$_6$H$_5$ |
| | 37 | 1-(4-Me)piperidino | CH$_3$ | C$_6$H$_5$ |
| | 39 | 1-hexamethyleneimino | CH$_3$ | C$_6$H$_5$ |

Several of the compounds of the present invention are active central nervous system stimulants or central nervous system depressants. Mice injected intraperitoneally with 0.1 ml/kg of a 0.6% suspension or solution of the compound in 0.5% METHOCEL$^R$ (Dow) and placed, individually, in clear plastic observation cages are observed to exhibit behavior indicative of such activity. Behavior characterized by hypoactivity, ptosis, passivity, and ataxia is indicative of depressant activity while hyperactivity, exopthalmous, and irritability are indicative of stimulant activity. Table IV indicates those compounds found to be active CNS depressants. Table V lists those compounds which are CNS stimulants.

Table IV

| CNS Depressants | | | | |
|---|---|---|---|---|
| Table | Example # | R | R' | R" |
| I | 5 | 1-(3-Me)piperidino | H | H |
| | 6 | 1-(4-Me)piperidino | H | H |
| | 8 | 1-hexamethyleneimino | H | H |
| II | 12 | 1-pyrrolidino | H | CH$_3$ |
| | 13 | 1-piperidino | H | CH$_3$ |
| | 16 | 1-(4-Me)piperidino | H | CH$_3$ |
| | 18 | 1-hexamethyleneimino | H | CH$_3$ |
| | 26 | 1-pyrrolidino | H | C$_6$H$_5$ |
| | 34 | 1-piperidino | CH$_3$ | C$_6$H$_5$ |

Table V

| CNS Stimulants | | | | |
|---|---|---|---|---|
| Table | Example # | R | R' | R" |
| I | 4 | 1-(2-Me)piperidino | H | H |
| | 7 | 1-(2,6-diMe)piperidino | H | H |
| | 9 | 1-heptamethyleneimino | H | H |
| II | 15 | 1-(3-Me)piperidino | H | CH$_3$ |
| | 17 | 4-morpholino | H | CH$_3$ |
| | 19 | 1-pyrrolidino | C$_2$H$_5$ | H |
| | 20 | 1-piperidino | C$_2$H$_5$ | H |
| | 22 | 1-(3-Me)piperidino | C$_2$H$_5$ | H |
| | 23 | 1-(4-Me)piperidino | C$_2$H$_5$ | H |
| | 25 | 1-hexamethyleneimino | C$_2$H$_5$ | H |
| | 26 | 1-pyrrolidino | H | C$_6$H$_5$ |
| | 27 | 1-piperidino | H | C$_6$H$_5$ |
| | 28 | 1-(2-Me)piperidino | H | C$_6$H$_5$ |
| | 33 | 1-pyrrolidino | CH$_3$ | C$_6$H$_5$ |
| | 35 | 1-(2-Me)piperidino | CH$_3$ | C$_6$H$_5$ |
| | 36 | 1-(3-Me)piperidino | CH$_3$ | C$_6$H$_5$ |
| | 37 | 1-(4-Me)piperidino | CH$_3$ | C$_6$H$_5$ |
| | 39 | 1-hexamethyleneimino | CH$_3$ | C$_6$H$_5$ |

In addition, many of the compounds are effective anti-convulsive agents and at a dosage of 60 mg/kg protect mice from convulsions when injected intraperitoneally with 0.1 ml/g of an 0.1% aqueous solution of HCl. For example, the following compounds were found effective, but are not to be construed to be the only compounds of the disclosed invention that are so active.

4-(4,5-dihydro-4-ethyl-2-oxazolyl)morpholine (Example 24)

1-(4,5-dihydro-5-phenyl-2-oxazolyl)-3-methyl-piperidine (Example 29)

4-(4,5-dihydro-4-methyl-5-phenyl-2-oxazolyl)morpholine (Example 3)

Sickle cell disease is an inherited form of chronic anemia in which a genetic defect causes sickle cell anemia patients to produce erythrocytes containing an abnormal form of hemoglobin known as Hbs. These abnormal hemoglobin molecules combine with one another in the deoxygenated state to form crystal-like structures. As a result, erythrocytes containing such hemoglobin are more rigid than normal cells and are thus less able to pass through small capillaries and terminal arterioles. This can cause clumping of the red cells and can seriously interfere with blood flow to vital organs. Agents which will inhibit the sickling of erythrocytes are therefore of potential clinical usefulness. Three compounds of the present invention have displayed anti-sickling activity in in-vitro dithionite tests. R. M. Nalbandian, et al, Clin. Chem. 17:1028-1032, 1971. They are:

4-(4,5-dihydro-2-oxazolyl)-morpholine (Table I, Example 4)

1-(4,5-dihydro-2-oxazolyl)-4-methylpiperidine (Table I, Example 8)

4-(4,5-dihydro-4-ethyl-2-oxazolyl)-morpholine (Table II, Example 26)

Some of the compounds display insecticidal properties which are useful in agricultural applications. For example the following compounds were found to be active in the control and killing of cabbage looper (*Trichoplusia ni*) when an aqueous dispersion of 400 ppm was applied to host plants infected with the cabbage looper.

4,5-dihydro-2-(1-pyrolidinyl)oxazoline (Example 2, Table I)

1-(4,5-dihydro-2-oxazolyl)-3-methylpiperidine (Example 5, Table I)

1-(4,5-dihydro-2-oxazolyl)-4-methylpiperidine (Example 6, Table I)

1-(4,5-dihydro-2-oxazolyl)-2,6-dimethylpiperidine (Example 7, Table I)

1-(4,5-dihydro-2-oxazolyl)hexahydro-1H-azepine (Example 8, Table I)

Some of the compounds also show antimicrobial activity. For example 4-(4,5-dihydro-2-oxazolyl)-morpholine (Example 4, Table I) was found to control *Ps. aeruginosa, P. mirabiles,* and *E. coli* incubated in urine collected from mice treated with 60 mg/kg of the compound.

We claim:

1. A 2-amino-2-oxazoline having the formula:

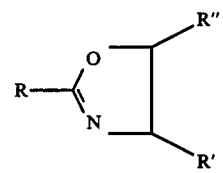

and the pharmaceutically-acceptable salts thereof wherein R is
1-pyrrolidino,
1-piperidino,
1-(2-methyl)piperidino,
1-(3-methyl)piperidino,
1-(4-methyl)piperidino,
4-morpholino, or
1-hexamethyleneimino;
R' is hydrogen or an alkyl group of from 1 to 4 carbon atoms; and R" is hydrogen, an alkyl group of from 1 to 4 carbon atoms, or phenyl with the proviso that when R' is hydrogen R" is other than hydrogen and when R' is alkyl R" is other than alkyl.

2. The 2-amino-2-oxazoline of claim 1 wherein R' is hydrogen and R" is methyl.

3. The 2-amino-2-oxazoline of claim 1 wherein R' is ethyl and R" is hydrogen.

4. The 2-amino-2-oxazoline of claim 1 wherein R' is hydrogen and R" is phenyl.

5. The 2-amino-2-oxazoline of claim 1 wherein R' is methyl and R" is phenyl.

6. The compound of claim 4 which is 4-(4,5-dihydro-5-phenyl-2-oxazolyl)morpholine.

7. The compound of claim 5 which is 1-(4,5-dihydro-4-methyl-5-phenyl-2-oxazolyl)piperidine.

8. The compound of claim 5 which is 1-(4,5-dihydro-4-methyl-5-phenyl-2-oxazolyl)hexamethyleneimine.

9. A 2-amino-2-oxazoline having the formula

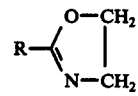

and the pharmaceutically-acceptable salts thereof wherein R is
1-pyrrolidino,
1-(2-methyl)piperidino,
1-(3-methyl)piperidino,
1-(4-methyl)piperidino,
4-morpholino,
1-hexamethyleneimino,
1-(2,6-dimethyl)piperidino, or
1-heptamethyleneimino.

10. The compound of claim 9 which is 1-(4,5-dihydro-2-oxazolyl)-2-methylpiperidine.

11. The compound of claim 9 which is 1-(4,5-dihydro-2-oxazolyl)-2,6-dimethylpiperidine.

12. The compound of claim 9 which is 1-(4,5-dihydro-2-oxazolyl)heptamethyleneimine.

* * * * *

UNITED STATES PATENT AND TRADEMARK OFFICE
CERTIFICATE OF CORRECTION

PATENT NO. : 4,064,348
DATED : December 20, 1977
INVENTOR(S) : Norton P. Peet, et al.

It is certified that error appears in the above-identified patent and that said Letters Patent are hereby corrected as shown below:

Column 2, line 30, formula should read as

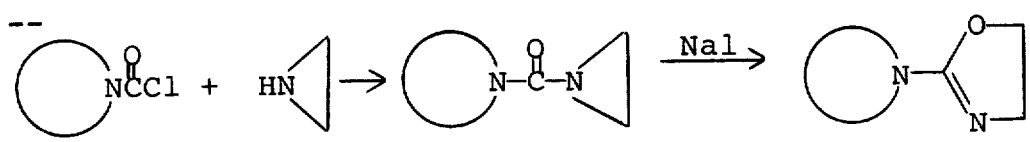

Column 2, line 50, formula should read as

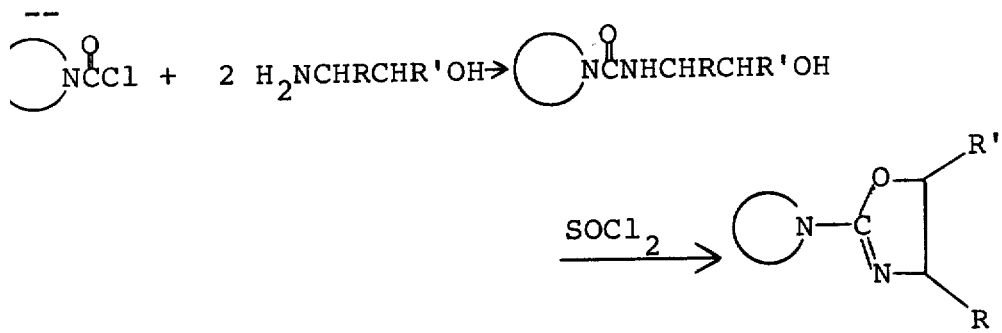

UNITED STATES PATENT AND TRADEMARK OFFICE
CERTIFICATE OF CORRECTION

PATENT NO.  : 4,064,348

DATED       : December 20, 1977

INVENTOR(S) : Norton P. Peet, et al.

It is certified that error appears in the above-identified patent and that said Letters Patent are hereby corrected as shown below:

Column 6, lines 30 - 50, Table II, Example No. 12, under the subheading Mol. Wt. should read --154.21--.

Column 6, Table II, Example No. 17, under the subheading Empirical Formula "$C_8H_{14}N_2O_2 170.21$" should read --$C_8H_{14}N_2O_2$--.

Column 6, Table II, Example No. 17, under the subheading Mol. Wt. should read --170.21--.

Signed and Sealed this

Twenty-fifth Day of April 1978

[SEAL]

Attest:

RUTH C. MASON
Attesting Officer

LUTRELLE F. PARKER
Acting Commissioner of Patents and Trademarks